(12) United States Patent
Wilson et al.

(10) Patent No.: US 8,135,449 B2
(45) Date of Patent: Mar. 13, 2012

(54) IMAGING OF OXYGEN BY PHOSPHORESCENCE QUENCHING

(75) Inventors: David F. Wilson, Philadelphia, PA (US); Sergei A. Vinogradov, Philadelphia, PA (US)

(73) Assignee: Oxygen Enterprises, Ltd., Philadelphia, PA (US)

( * ) Notice: Subject to any disclaimer, the term of this patent is extended or adjusted under 35 U.S.C. 154(b) by 901 days.

(21) Appl. No.: 11/661,765

(22) PCT Filed: Aug. 26, 2005

(86) PCT No.: PCT/US2005/030344
§ 371 (c)(1), (2), (4) Date: Jul. 24, 2008

(87) PCT Pub. No.: WO2006/026396
PCT Pub. Date: Mar. 9, 2006

(65) Prior Publication Data
US 2009/0082650 A1    Mar. 26, 2009

Related U.S. Application Data

(60) Provisional application No. 60/604,665, filed on Aug. 26, 2004.

(51) Int. Cl.
*A61B 5/1455* (2006.01)

(52) U.S. Cl. .......... 600/310; 600/317; 600/473
(58) Field of Classification Search .......... 600/310, 600/322, 317, 364, 311, 312; 422/82.05
See application file for complete search history.

(56) References Cited

U.S. PATENT DOCUMENTS

| | | | |
|---|---|---|---|
| 4,947,850 A | 8/1990 | Vanderkooi | |
| 5,127,405 A | 7/1992 | Alcala | |
| 5,837,865 A | 11/1998 | Vinogradov | |
| 6,274,086 B1 * | 8/2001 | Wilson et al. | 422/82.08 |
| 6,701,168 B1 | 3/2004 | Wilson | |

* cited by examiner

*Primary Examiner* — Eric Winakur
(74) *Attorney, Agent, or Firm* — Montgomery, McCracken, Walker & Rhoads, LLP; Evelyn H. McConathy

(57) ABSTRACT

A method of real-time imaging of dissolved oxygen concentration, comprising adding an oxygen-quenched phosphorescent composition to a sample, exciting phosphorescence in the composition by illuminating the sample with pulses of light, detecting phosphorescence intensity as a function of position in the sample at first and second times following exciting pulses of light, determining oxygen concentration from the phosphorescence detected at the first and second times, generating an image of the oxygen concentration as a function of position, and repeating the exciting, detecting, determining, and image generating steps to produce a series of images showing the oxygen concentration varying over time.

20 Claims, 3 Drawing Sheets

IMAGING OF OXYGEN BY PHOSPHORESCENCE QUENCHING

CROSS REFERENCE TO RELATED APPLICATIONS

This application claims the benefit of U.S. Provisional Application No. 60/604,665, filed Aug. 26, 2004, which is incorporated herein by reference in its entirety.

BACKGROUND OF THE INVENTION

It has previously been shown that dissolved oxygen in biological fluids can quench the phosphorescence of certain phosphorescent molecules exposed to the fluids, and that it is possible to measure the oxygen concentration by measuring the quenching of phosphorescence. Oxygen quenching may be used, for example, for the non-invasive (apart from the injection of a solution of the phosphorescent agent), quantitative determination of oxygen pressure in the vasculature of tissue in vivo. Commonly invented and assigned U.S. Pat. No. 5,837,865 (Vinogradov et al.) discloses phosphorescent molecules that can be used for imaging of the distribution of dissolved oxygen by imaging the phosphorescence of the molecules when exposed to a suitable source of exciting light.

Oxygen quenching reduces both the intensity and the phosphorescence lifetime or decay time of the phosphorescent light. Commonly invented and assigned U.S. Pat. No. 6,701,168 (Wilson et al.) describes a method of measuring the phosphorescence lifetime by the "phase method" in which a phosphorescent sample is repeatedly excited with a periodic pulsed light source. Each pulse of exciting light causes a pulse of phosphorescence, delayed slightly after the exciting pulse. Thus, the periodic exciting pulse train causes a periodic phosphorescent pulse train at the same frequency, but wherein each pulse is delayed. The delay time, which is a measure of the phosphorescence lifetime, is observed as a phase shift between the two pulse trains.

U.S. Pat. No. 5,127,405 (Alcala et al.) describes a process for determining the intensity/time curve of the phosphorescence in which the sample is excited with a periodic pulsed light source and the detected phosphorescence is measured briefly at intervals slightly greater than the period of the exciting light source. Assuming that all exciting pulses and all phosphorescence pulses are identical, each successive measurement measures the intensity of the phosphorescence at a slightly later time after the exciting pulse, enabling the intensity/time curve to be reconstructed.

Both the methods of the Wilson '168 patent and the method of Alcala rely on combining measurements from a substantial number of successive pulses to form a single image with a time dimension. As a result, these methods can produce results only after a delay. These methods rely on the assumption that the system under observation does not change during the period of observation. Thus, there has, until the present invention, been a need for a method and system for monitoring phosphorescence quenching that can produce accurate images in real time showing a system changing during the period of observation.

SUMMARY OF THE INVENTION

According to one embodiment of the present invention, there is provided a method of real-time imaging of dissolved oxygen concentration in a sample, comprising adding to a sample an oxygen-quenched phosphorescent substance, exciting phosphorescence in the phosphorescent substance by illuminating the sample with pulses of light, detecting phosphorescence as a function of position in the sample at first and second times following exciting pulses of light, determining oxygen concentration from the phosphorescence detected at the first and second times, generating an image of the oxygen concentration as a function of position, and repeating the exciting, detecting, determining, and image generating steps to produce a series of images showing the oxygen concentration varying over time.

According to another embodiment of the invention, there is provided an apparatus for real-time imaging of dissolved oxygen concentration in a sample, comprising a light source for exciting phosphorescence in a phosphorescent substance by illuminating the sample with pulses of light, a detector for detecting phosphorescence as a function of position in the sample at first and second times following an exciting pulse of light, a processor arranged to determine a difference between the phosphorescence detected at the first time and the phosphorescence detected at the second time, and a display unit arranged to generate an image of a function of the determined difference as a function of position, wherein the detector, processor, and display unit are arranged to generate successive images at successive times.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE DRAWINGS

For the purpose of illustrating the invention, there are shown in the drawings various forms that are presently preferred; it being understood, however, that this invention is not limited to the precise arrangements and constructions particularly shown.

DETAILED DESCRIPTION OF CERTAIN EMBODIMENTS OF THE INVENTION

Figure 1:
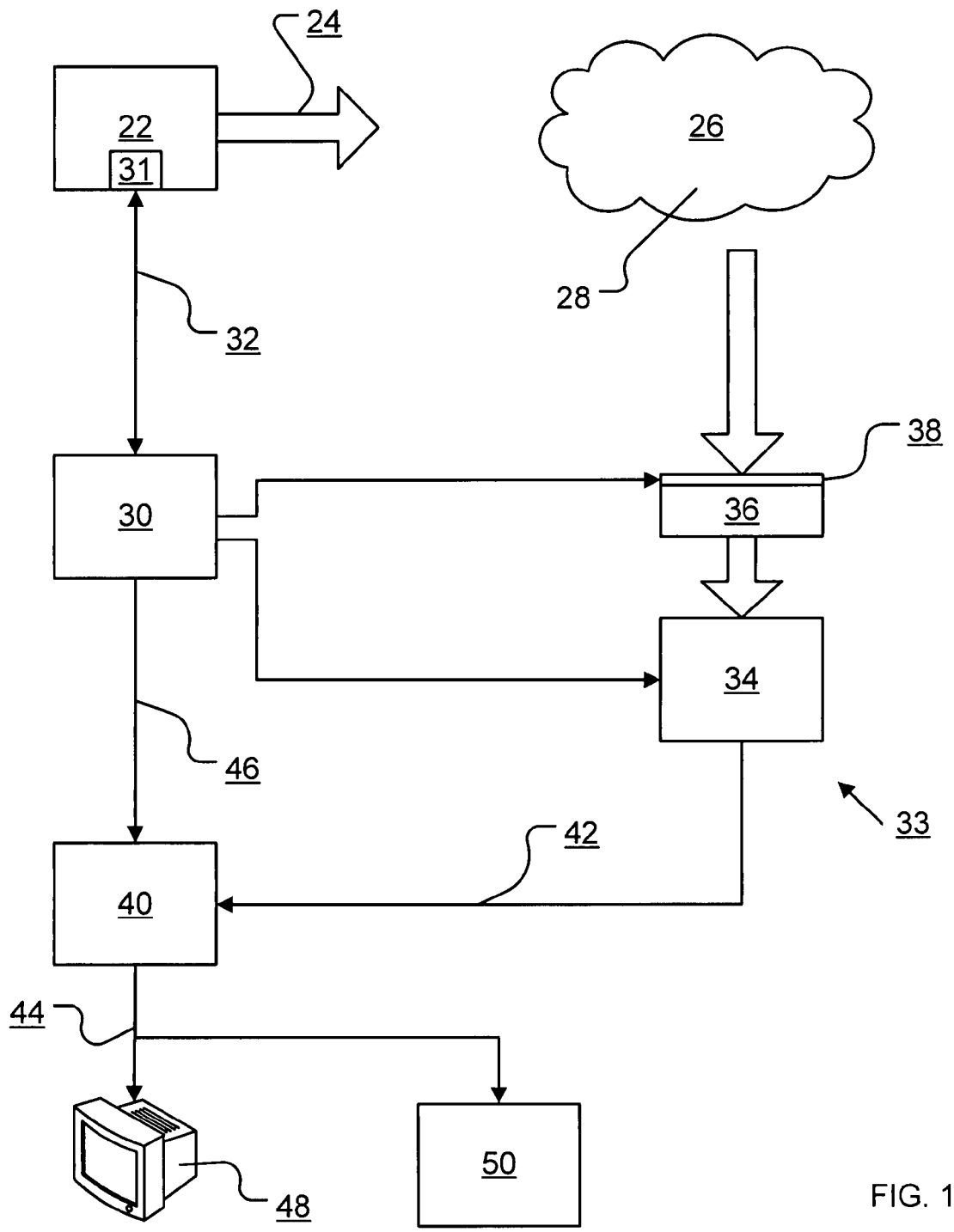
FIG. 1 is a block diagram of a first form of system according to the invention.

Referring now to the drawings, wherein like reference numerals identify like elements, components, subassemblies etc., FIG. 1 depicts an embodiment of a real-time oxygen imaging device according to the invention, indicated generally by the reference numeral 20.

The imaging device 20 comprises a light source 22 that in use directs light 24 at a sample 26. In a practical implementation the sample 26 contains dissolved oxygen with a distribution that varies both as a function of ion within the sample and as a function of time. For example, the sample 26 may be tissue in vivo, such as vasculature within which blood or other oxygen-carrying liquid circulates. The sample contains a phosphorescent composition 28 that exhibits quenching of phosphorescence by dissolved oxygen. Phosphorescent composition 28 may be any one of, or a combination of, the water-soluble phosphorescent compositions disclosed in the above-mentioned U.S. Pat. No. 5,837,865 (Vinogradov et al.), which is incorporated herein by reference in its entirety. Alternatively, phosphorescent composition 28 may be another phosphorescent material suitable for use herein and compatible with sample 26. Many such substances are known, and may be referred to as a "dye" or as a "marker," depending on application. In the interests of conciseness, substance 28 is referred to herein simply as a "phosphorescent composition," although combinations of such compositions may also occur, and thus are also included herein within that term. Light source 22 may be selected to emit light of a specific frequency that excites phosphorescence in phosphorescent composition 28.

The light source 22 shown in FIG. 1 is a flash lamp that repeatedly emits a short flash of light 24 in coordination with a controller 30, which may be a microcomputer. Flash lamp 22 may be arranged to emit a flash of light 24 in response to a clock signal from controller 30, or flash lamp 22 may have an internal clock 31 that causes flash lamp 22 to emit flashes of light at regular intervals. When flash lamp 22 has internal clock 31, timing signals 32 are sent between internal clock 31 and controller 30. Controller 30 may either control the timing of flash lamp 22 or passively receive timing information from flash lamp 22.

As will be explained in more detail below, in the embodiment shown in FIG. 1, the duration of flashes of light 24 is not important. In order to allow rapid cycling of imaging device 20, the duration of flashes of light 24 may be smaller than the phosphorescence lifetime of phosphorescent composition 28. The cutoff at the end of each flash of light 24 is sharp-edged to within a small fraction of the phosphorescence lifetime of phosphorescent composition 28, and the timing of the cutoff is known to controller 30 to a small fraction of the phosphorescence lifetime of phosphorescent composition 28. When a single timing signal 32 is sent between controller 30 and flash lamp 22 for each flash of light 24, controller 30 may be programmed with the timing signal 32 to the end of flash of light 24.

Sample 26 is observed by a camera 33. In FIG. 1, camera 33 is an intensified charge-coupled device (CCD) camera 34, in which the intensifier is a gated micro-channel array (MCA) 36 with a gate 38. CCD camera 34 and gate 38 are controlled by controller 30. Controller 30 can open and close gate 38, and can cause CCD camera 34 to start and stop its imaging and readout phases, in coordination with the timing of flash lamp 22. In imaging device 20 shown in FIG. 1, controller 30 can open gate 38 at a precisely controlled delay time after the end of flash of light 24. As will be further explained below, controller 30 may vary the delay time in a repeating pattern, to produce groups of two or more images having different delay times within each group and having the same delay times repeated for successive groups.

Images from CCD camera 34 are sent to image processor 40. Image processor 40 may be embodied in the same physical computer as controller 30. Alternatively, image processor 40 may be a separate device optimized for parallel processing of image pixels. Image processor 40 is arranged to receive a stream of camera images 42 from CCD camera 34, compare successive images 42, and generate a final image 44 showing a difference between successive images. Image processor 40 may include image stacking software arranged to recognize shape features recurring in successive images, and to distort the images slightly so that the shape features coincide exactly. Such software is widely available and, in the interests of conciseness, will not be further discussed here.

Image processor 40 may operate independently of controller 30. Alternatively, image processor 40 may receive a synchronizing signal 46 from controller 30. When controller 30 is generating groups of images, controller 30 may send synchronizing signal 46 to tell processor 40 when each group begins. Absent synchronizing signal 46, if processor 40 were to become out of phase with controller 30, so that images were no longer correctly grouped and compared, erroneous data could result.

Image processor 40 sends difference image 44 to display 48, and may also send difference image 44 to recording device 50 for later viewing. Display 48 may display successive images at a normal video rate, typically 30 frames per second in the U.S., or 25 frames per second in Europe. When each difference image 44 is formed from a group of two camera images 42, and each camera image 42 is grouped with both the immediately preceding and the immediately following camera image 42 to form two successive difference images 44. Flash lamp 22 and camera 33 are then operating at the same rate, e.g., in the embodiment utilizing 25 or 30 images per second, as display 48. By this method, faster image rates are possible and a technically more robust presentation is provided. Faster image rates allow more than two camera images 42 to be grouped for each difference image 44, and/or allow one to monitor video rates more rapidly than 25 or 30 frames per second, either of which may improve the quality of the imaging. Faster image rates may also allow slow-motion video to be produced.

Figure 2:
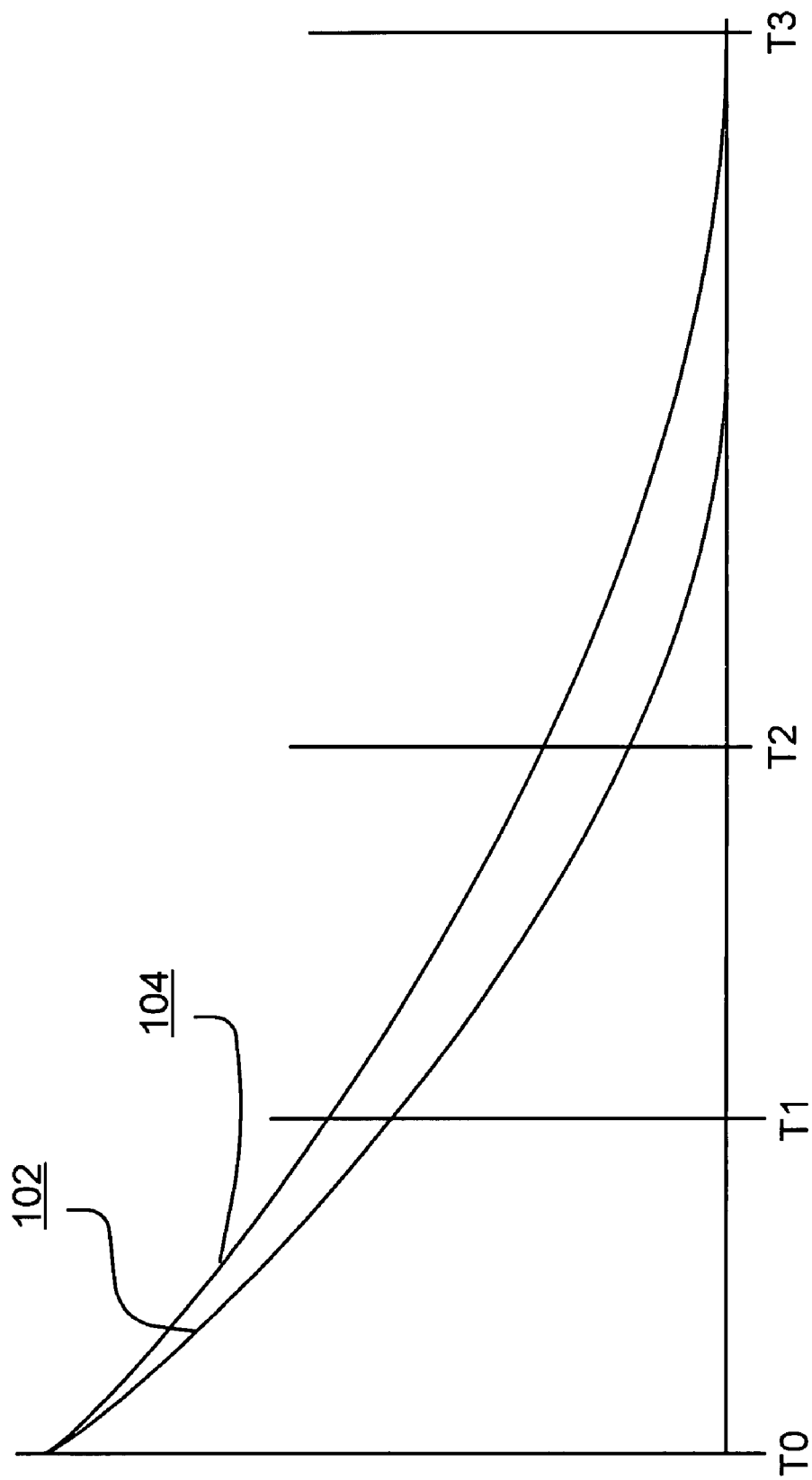
FIG. 2 is a graph showing the effect of oxygen on the intensity of phosphorescence decay with regard to time.

Referring now also to FIG. 2, when excitation of a phosphorescent composition ceases at time T0, the intensity of phosphorescence decays roughly exponentially over time. Oxygen quenching shortens the phosphorescence lifetime, so the intensity curve 102 with quenching decays more rapidly than the intensity curve 104 without quenching. The shape of intensity curve 102 depends on the degree of quenching, and thus on the oxygen concentration. In an embodiment of a process using imaging device 20, gate 38 may be opened, for example, at time T1 or time T2, and may remain open until time T3. The imaging phase of CCD camera 34 then commences no later than time T1, and ends no earlier than time T3. The readout phase of CCD camera 34 then commences no earlier than time T3 and ends before time T1 of the next cycle. Thus, the light intensity recorded by CCD camera 34 in each camera image 42 corresponds to the area under the curve 102 or 104 between times T1 and T3 or between times T2 and T3. Time T3 may be selected as a time sufficiently late in the decay of intensity curves 102, 104 that the area under the curves after time T3 is not significant. The exact timing of time T3 is then not important.

As may be seen from FIG. 2, provided that the time periods T1-T0 and T2-T0 are appropriate and are known, the phosphorescence lifetime $\tau$ can be estimated from the ratio of the light intensities for an exposure starting at T1 and an exposure starting at T2. Because phosphorescence decay curves 102, 104 are approximately exponential, a plot of the logarithm of intensity against time is a straight line with a gradient equal to $1/\tau$. The measured intensities can be converted to logarithms with a standard look-up table, and the gradient calculated arithmetically. It is not necessary to know an absolute value for the intensity of the phosphorescence. Provided that the quenching characteristic for phosphorescent composition 28 is known, the degree of quenching, and therefore the oxygen concentration, can be estimated from the phosphorescence lifetime using the Stern-Volmer equation. Thus, imaging device 20 shown in FIG. 1 makes it possible to generate a measurement of oxygen concentration in sample 26 from as few as two successive images of sample 26.

Figure 3:
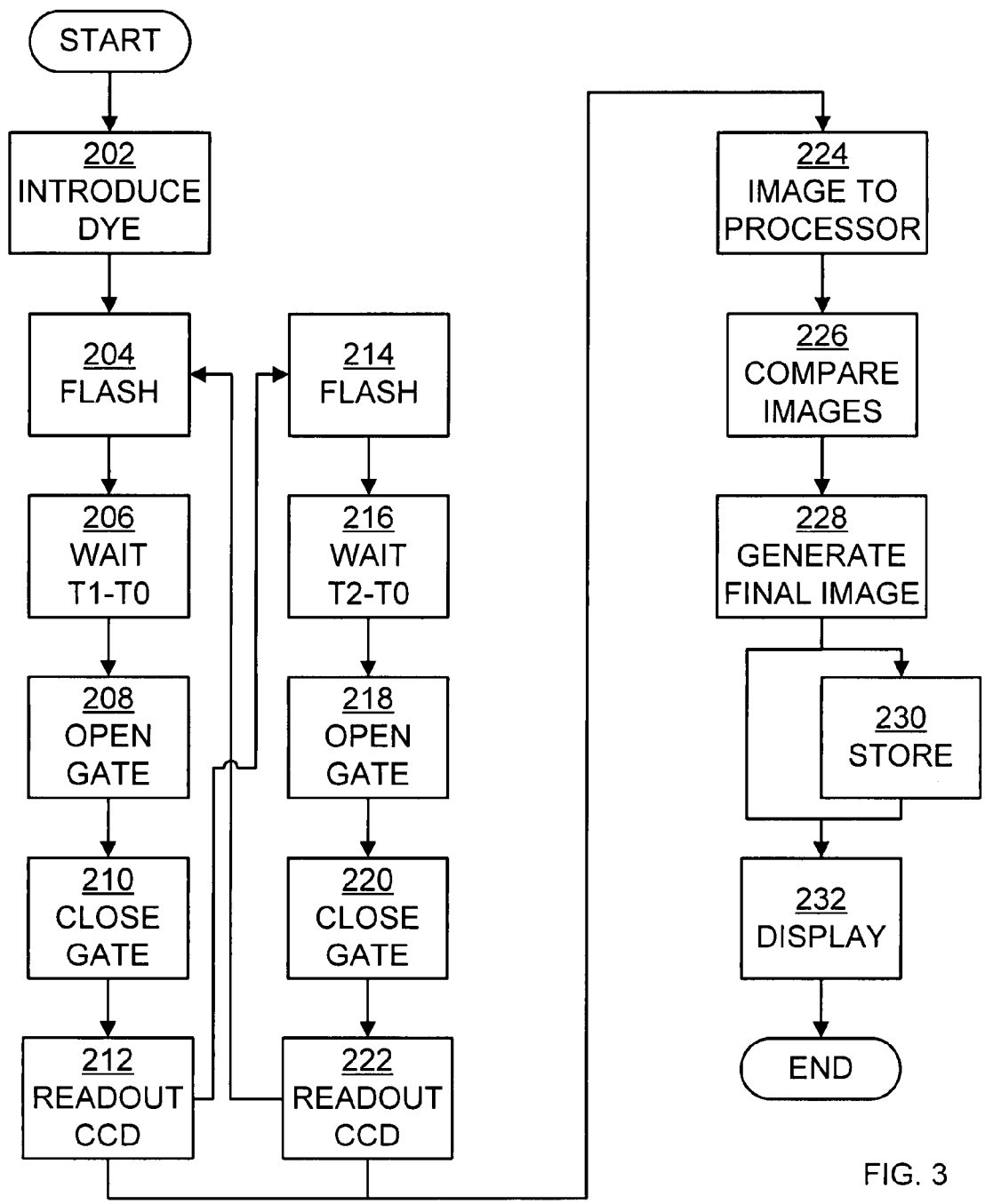
FIG. 3 is a flow chart of an embodiment of a method according to the invention.

Referring now to FIG. 3, in one embodiment of a method according to the invention, in step 202 a sample 26 is prepared, including introducing a suitable phosphorescent composition 28. In step 204, sample 26 is exposed to a flash of light 24 from flash lamp 22. Flash of light 24 may be sufficiently intense, and sufficiently long in duration, to substantially saturate the excited state of phosphorescent composition 28. Once phosphorescent composition 28 is saturated, continued illumination maintains a steady state, in which case the phosphorescent composition decays (thereby emitting light) and is re-excited. The duration of such a steady illuminated and saturated state does not greatly affect the process shown in FIG. 3. However, once flash of light 24 ends, the phosphorescence decays as shown in FIG. 2. In step 206, a controlled delay corresponding to the time T1-T0 is imposed from the end of the flash of light 24 before gate 38 of MCA intensifier 36 is opened (step 208). In step 210, at time T3, gate 38 is closed again. In step 212, camera image 42 is read, as received by CCD camera 34 in the period between step 208 to step 210.

The process then proceeds to step 214, wherein sample 26 is exposed to another flash of light 24 from flash lamp 22. In step 216, a controlled delay corresponding to the time T2-T0 is imposed from the end of the flash of light 24 before gate 38 of MCA intensifier 36 is opened (step 218). In step 220, at time T3, gate 38 is closed again. In step 222, camera image 42 is read, as received by CCD camera 34 in the period between step 218 to step 220. Steps 214-222 may be substantially the same as steps 204-212, except for the different delay time at steps 206 and 216.

The process then loops back to step 204, wherein sample 26 is exposed to another flash of light 24 from flash lamp 22. As is shown symbolically by the figure-8 loop in FIG. 3, the process then continues as long as desired through a cycle of flash, image, and readout, with the delay between the end of the flash of light 24 and the opening of gate 38 being alternately T1-T0 and T2-T0.

The loop rate may be chosen by the user. In order to reduce noise, gate 38 may be closed, and read-out step 212, 222 started, as soon as the unquenched phosphorescence curve 104 has dropped to a level at which the area under the remaining tail of the curve is negligible at the desired precision of imaging. Gate 38 may be closed even sooner, if the response time of gate 38 permits, and provided the areas under curves 102, 104 allow quenching to be determined to a desired level of precision. As may be seen from FIG. 2, it is presently believed the optimum timing for time T3 is close to the point at which unquenched phosphorescence curve 104 decays to negligible intensity. Cycle time may be slightly shortened by allowing the end of readout phase 212, 222 to overlap with the next flash of light 24 in subsequent step 214, 204.

When the times taken between step 204 and step 212, and between step 214 and step 222, are less than the desired cycle time, a pause may occur before steps 204 and 214. When monitor 48 is viewed in real-time by a human observer, the video frame rate may be, preferably 25 to 30 frames per second, which is to say that there may be at least 25 to 30 cycles of the figure-8 loop of steps 204 through 222 per second, thereby avoiding a flickering or jerky image. Since the frame rate is a function of the rate of change in the field of view, a slower change allows for slower frame rates. The preferred video frame rate may be a function of the rate of change in the field of view of sample 26. When conditions in sample 26 change rapidly over time, the cycle time may be short enough that sample 26 does not change appreciably within one cycle, to avoid the image being obscured by artifacts resulting from changes in sample 26 between consecutive camera images 42.

In step 224, camera images 42 read out from CCD camera 34 in steps 212, 222, are sent to processor 40, which saves the first image of a group until a second image is received. In step 226, processor 40 compares consecutive images 42 from step 212 and 222, and generates a final image 44 that shows how the two camera images 42 differ. As explained above, by measuring the ratio of the intensities of phosphorescent light in image 42 from step 212, and image 42 from step 222, a measure of the amount of quenching of the phosphorescence lifetime, and thus of the dissolved oxygen concentration in sample 26, can be obtained without needing to determine an absolute level of phosphorescence. By aligning image 42 from step 212, and image 42 from step 222, and by calculating the ratio separately for each pixel in step 228 an image 44 of the oxygen concentration can be rapidly generated.

In an embodiment of the process shown in FIG. 3, each camera image 42 from step 212 is compared with both the immediately preceding and the immediately following camera image from step 222, to produce two successive final images 44. This process can improve the signal to noise ratio at display 48 as compared with a process in which each camera image 42 contributes to a single final image 44. In addition, if there is any change in sample 26 between successive camera images 42, the change may appear as an artifact in final image 44. When the change in sample 26 continues over several cycles, by generating successive final images 44 using a camera image 42 from step 212 that is alternately earlier and later in time than the camera image 42 from step 222, the sign of the artifact alternates, and the artifacts are largely canceled out, leaving only a (usually slight) increase in noise. Using each camera image 42 for two video frames may also reduce jerkiness at low imaging rates.

In step 230, image 44 is sent to a storage device 50 for future reference. In step 232, image 44 is sent to monitor 48, and is displayed for viewing by a user. By repeating steps 226, 228, and 232 every time a pair of camera images 42 are received at processor 40, a real-time video display of oxygen concentration in sample 26 is produced on monitor 48. As is shown in FIG. 3, alternatively, or in addition, images 44 from storage device 50 may be fed to monitor 48, allowing viewing of the video display at a later time, or allowing buffering of the real-time video to permit action replays, slow motion, and other close reviews of interesting parts of the video.

As may be seen from FIG. 3, image processing steps 224 through 232 do not need to be synchronized with imaging steps 204 through 222. Thus, the time taken for steps 226 and 228 may be determined by the user, depending on how much time lag is acceptable before the video image appears on monitor 48 and how much image processing power is available for processor 40. The illuminating step 204 of one cycle may occur before video frame 44 from the previous cycle appears on monitor 48, or even before comparing step 226 is completed for the previous pair of camera images 42. For example, when a user wishes to vary conditions of a test or experiment in real time, using the effect on the oxygen concentration of the condition being varied to guide further variation, the time lag may be kept small, as compared with the response time of the system under test or experiment.

While imaging device 20 has been described in terms of embodiments that exemplify an anticipated use and application thereof, other embodiments are contemplated which also fall within the scope and spirit of the invention. For example, light source 22 has been described as a flash lamp. Light source 22 may instead be another form of light source, such as one that produces short, intense pulses of light, for example, a light emitting diode, a diode laser, a pulsed laser, or the like. When light source 22 is a laser or other light source with a narrow frequency band, a peak emission frequency selected to match the peak excitation frequency of phosphorescent composition 28 may be selected. Camera 33 may be arranged, either by filtering or by selection of the photosensitive elements that receive light from sample 26, to have a peak sensitivity corresponding to the peak emission frequency of phosphorescent composition 28.

By way of example, suitable values of T1-T0, T2-T0, and T3-T0 for the phosphorescent compositions mentioned in U.S. Pat. No. 5,837,865 (Vinogradov et al.) may be 20 μs, 40 μs, and 2.5 ms. The cycle time for each camera image 42 may be 3.3 ms. It is then possible to take as many as ten camera images 42 for each final image or video frame 44, while maintaining a video frame rate of 30 frames per second, or to achieve a video frame rate of 150 frames per second with two camera images 42 for each video frame 44.

In the process shown in FIG. 3, each video frame or final image 44 is generated from two consecutive camera images 42. By using both the prior and following images (in the sequence a, b, c, d, e, f, for example, the display is b/a, b/c, d/c, d/f, etc) the result is to increase the frame rate for the display so that it is equal to the imaging rate. As a result, in this example, the noise on the display in the exemplary sequence is, thus, decreased by the square root of 2.

More importantly, in the past there typically has been a systematic difference in time between when the images were taken. This time difference resulted in movements in the visual field that generated persistent artifacts that seriously degraded the ability to see differences in oxygen pressure. The present method, however, e.g., in the presentation of b/a, b/c, d/c, etc is designed to eliminate the systematic time difference between images and thus eliminate movement artifacts. Although the movement will still create artifacts, they will be of opposite signs in images displayed one after the other, such as b/a and b/c. As a result, they will appear only as an increase in the apparent "noise" in the oxygen images. In this mode, averaging methods, such as, displaying a running average of 3 or 5 images, can be used to suppress the movement induced noise, whereas such averaging would otherwise only have made the movement artifacts worse for the simple a/b, b/c, etc mode. Consequently, the present approach will give much better performance in all cases, having fewer artifacts, when there is a need to scan a heterogeneous field, such as in all types of endoscopy.

In the alternative, one video frame 44 may be generated from three or more camera images 42. Camera images 42 may then be generated by opening gate 38 at three or more different times T1, T2, etc. Processor 40 is then provided with a more accurate representation of actual intensity/time curve 102, 104, which may improve the accuracy of quenching values, and thus of oxygen concentration values. Alternatively, or in addition, one video frame 44 may be generated from three or more camera images 42 including two camera images 42 generated by opening gate 38 at the same time T1, T2, etc. By combining notionally identical images 42, noise in the final image 44 may be reduced. Notionally identical camera images may be combined by repeatedly exposing CCD camera 34 to phosphorescence from successive flashes of light 24 at the same gate opening time T1, T2, without reading out camera image 42, so that charge accumulates in CCD camera 34. Alternatively, notionally identical camera images 42 may be read out from CCD camera 34 and stacked electronically in processor 40.

In the process described above with reference to FIG. 3, each camera image 42 is paired with both the immediately preceding image 42 and the immediately following image 42 to produce two consecutive video frames 44. Alternatively, each two consecutive camera images 42 may contribute to one video frame 44.

In the process shown in FIG. 3, camera images 42 taken with gate 38 opening at time T1 alternate strictly with images taken with gate 38 opening at time T2. Strict alternation is not necessary, provided that at least two images with different opening times are available for generation of each video frame 44. When images at T1 and images at T2 do alternate, either image may be taken first.

Depending on the specific phosphorescent composition used, the light may be visible light, or it may be, for example, infrared light or near infrared light.

Further, a variety of other modifications to the embodiments will be apparent to those skilled in the art from the disclosure provided herein. Thus, the present invention may be embodied in other specific forms without departing from the spirit or essential attributes thereof and, accordingly, reference should be made to the appended claims, rather than to the foregoing specification, as indicating the scope of the invention.

What is claimed is:

1. A method of imaging of dissolved oxygen concentration in a sample, comprising:
adding to a sample an oxygen-quenched phosphorescent substance,
exciting phosphorescence in the phosphorescent substance by illuminating the sample with pulsed light,
detecting phosphorescence intensity as a function of position in the sample at first and second times following an exciting pulse of light,
determining oxygen concentration from the phosphorescence detected at the first and second times,
generating an image of the oxygen concentration as a function of position, and
repeating the exciting, detecting, determining, and image generating steps to produce a series of images showing the oxygen concentration over time.

2. The method of claim 1, wherein detecting phosphorescence intensity at the first and second times comprises detecting phosphorescence over a period starting at a first time after an exciting pulse and a period starting at a second time after an exciting pulse.

3. The method of claim 2, wherein detecting phosphorescence intensity at the first and second times comprises integrating the phosphorescence detected over the period starting at the first time and over the period starting at the second time.

4. The method of claim 1, wherein detecting phosphorescence intensity at the first and second times following an exciting pulse of light comprises detecting phosphorescence at a first time following a first exciting pulse of light and detecting phosphorescence at a second time following a second exciting pulse of light.

5. The method of claim 4, wherein the first and second exciting pulses of light are successive pulses of light in a periodic stream of pulses, and repeating the exciting step comprises illuminating the sample with further pulses in the periodic stream of pulses.

6. The method of claim 5, wherein the first and second exciting pulses of light are consecutive pulses of light in the periodic stream of pulses, repeating the detecting step comprises detecting phosphorescence intensity at the first time following a third pulse consecutively following the second exciting pulse, and repeating the determining step comprises determining oxygen concentration from the phosphorescence detected at the first time following the third pulse and at the second time following the second pulse.

7. The method of claim 1, further comprising carrying out the repeating step at least 25 times a second.

8. The method of claim 1, wherein the exciting step of the repeating step begins before the previous image generating step is completed.

9. The method of claim 7 wherein the exciting step of the repeating step begins before the previous determining step is completed.

10. Apparatus for real-time imaging of dissolved oxygen concentration in a sample, comprising:
- a light source for exciting phosphorescence in a phosphorescent substance by illuminating the sample with pulses of light;
- a detector for detecting phosphorescence as a function of position in the sample at first and second times following an exciting pulse of light;
- a processor arranged to determine a difference between the phosphorescence intensity detected at the first time and the phosphorescence detected at the second time; and
- a display unit arranged to generate an image of a function of the determined difference as a function of position;
- wherein the detector, processor, and display unit are arranged to generate successive images at successive times.

11. The apparatus of claim 10, wherein the detector is arranged to detect phosphorescence over a first period starting at the first time after an exciting pulse and over a second period starting at the second time after an exciting pulse.

12. The apparatus of claim 11, wherein the detector is arranged to integrate the phosphorescence detected over the first period and to integrate the phosphorescence detected over the second period.

13. The apparatus of claim 10, wherein the detector is arranged to detect phosphorescence at the first time following a first exciting pulse of light and at the second time following a second exciting pulse of light.

14. The apparatus of claim 10, wherein the detector comprises an intensified charge-coupled device (CCD) camera, and the first and second times are controlled by gating the intensifier.

15. The apparatus of claim 10, wherein the light source is arranged to emit a periodic stream of pulses and the detector is arranged to detect phosphorescence intensity from successive pulses of light in the periodic stream.

16. The apparatus of claim 15, wherein the detector is arranged to detect phosphorescence at the first and second times following pairs of pulses in the periodic stream of pulses wherein the second pulse of a pair of pulses is the first pulse of a subsequent pair of pulses.

17. The apparatus of claim 10, wherein the detector, processor and display unit are arranged to produce a new image at least 25 times a second.

18. The apparatus of claim 10, wherein the detector is arranged to start detecting phosphorescence for a next image before the processor has completed determining the difference for the previous image.

19. The apparatus of claim 10, wherein the light source is arranged to emit light with a peak intensity at a frequency selected to excite an oxygen-quenched phosphorescent composition.

20. The apparatus of claim 10, wherein the detector is arranged to detect light with a peak frequency sensitivity selected to correspond to a peak emission frequency of an oxygen-quenched phosphorescent composition.

* * * * *